United States Patent
Levy

(10) Patent No.: US 6,613,519 B1
(45) Date of Patent: *Sep. 2, 2003

(54) METHOD OF DETERMINING A RISK OF HYPERGLYCEMIC PATIENTS OF DEVELOPING A CARDIOVASCULAR DISEASE

(75) Inventor: Andrew P. Levy, Kiryat Shmuel (IL)

(73) Assignee: Rappaport Family Institute for Reseach in the Medical Sciences, Haifa (IL)

(*) Notice: Subject to any disclaimer, the term of this patent is extended or adjusted under 35 U.S.C. 154(b) by 11 days.

This patent is subject to a terminal disclaimer.

(21) Appl. No.: 09/815,016

(22) Filed: Mar. 23, 2001

Related U.S. Application Data

(63) Continuation-in-part of application No. 09/556,469, filed on Apr. 20, 2000, now Pat. No. 6,251,608.
(60) Provisional application No. 60/273,538, filed on Mar. 7, 2001.

(51) Int. Cl.$^7$ .............................. C07H 21/04; C12Q 1/68
(52) U.S. Cl. ........................... 435/6; 435/7.1; 435/91.1; 536/23.1
(58) Field of Search ........................... 435/6, 91.1, 7.1; 536/23.1

(56) References Cited

U.S. PATENT DOCUMENTS 6,251,608 B1 * 6/2001 Levy ................................ 435/6
6,325,999 B1 * 12/2001 Bellgrau et al. ........... 424/93.21
6,380,191 B1 * 4/2002 Desai et al. ................ 514/236.8

FOREIGN PATENT DOCUMENTS

WO    WO 98/37419    * 8/1998 .......... G01N/33/68

OTHER PUBLICATIONS

Prabha et al "Haptoglobin patterns in essential hypertension and associated conditions—increase risk for Hp (2–2)" Hum. Hered. vol. 37, p. 345–348, 1987.*
Chandra et al "Haptoglobin Phenotypes in Diabetes mellitus and Diabetic Retinopathy" Hum. Hered. vol. 41, p. 347–350, 1991.*
Delanghe et al "Haptoglobin polymorphism and peripheral arterial occlusive disease" Atherosclerosis, vol. 145, p. 287–292, 1999.*
Langlois et al "Biological and clinical significance of haptoglobin polymorphism in humans" Clinical Chemistry, vol. 42, No. 10, p. 1589–1600, 1996.*
Sehajpal et al. "Genetic Polymorphisms in Cardiovascular Diseases". Acta Anthropogenetica. vol. 3, No. 3&4, pp. 219–224, 1979.*
Delanghe et al. "refractory hypertension is associated with the haptoglobin 2–2 phenotype". J. of Cardiovascular Risk. vol. 2, No. 2, p. 131–136, Apr. 19950.*

* cited by examiner

Primary Examiner—Jeffrey Fredman
Assistant Examiner—Jeanine Goldberg
(74) Attorney, Agent, or Firm—G. E. Ehrlich (1995) Ltd.

(57) ABSTRACT

A method and kit of evaluating a risk of a diabetic patient to develop cardiovascular disease (CVD) is disclosed. The method comprises determining a haptoglobin phenotype of the diabetic patient and thereby evaluating the risk of the diabetic patient to develop the cardiovascular disease (CVD), wherein the risk is decreased in diabetic patients with haptoglobin 1-1 phenotype as compared to patients with haptoglobin 1-2 or haptoglobin 2-2 phenotypes. The risk is also decreased in diabetic patients with haptoglobin 1-2 phenotype as compared to patients with haptoglobin 2-2 phenotype. The kit comprises packaged reagents for determining a haptoglobin phenotype of the diabetic patient and the kit is identified for use in evaluating a risk of a diabetic patient to develop cardiovascular disease (CVD).

11 Claims, No Drawings

METHOD OF DETERMINING A RISK OF HYPERGLYCEMIC PATIENTS OF DEVELOPING A CARDIOVASCULAR DISEASE

This is a continuation-in-part of U.S. patent application Ser. No. 09/556,469, filed Apr. 20, 2000 now U.S. Pat. No. 6,251,608. This Application also claims the benefit of priority from U.S. Provisional Patent Application No. 60/273,538, filed Mar. 7, 2001.

FIELD AND BACKGROUND OF THE INVENTION

The present invention relates to a method of determining a risk of hyperglycemic patients of developing cardiovascular disease.

Cardiovascular disease (CVD) is the most frequent, severe and costly complication of type 2 diabetes.[1] It is the leading cause of death among patients with type 2 diabetes regardless of diabetes duration.[2] Several population-based studies have consistently shown that the relative risk of CVD in diabetic individuals is several fold higher compared to those without diabetes.[3-7] This increased risk appears to be even more striking in women.[4,5,8] Risk factors such as hypertension, hyperlipidemia and cigarette smoking all independently increase the relative risk of the diabetic patient of developing CVD, but the effect of diabetes appears to be independent of conventional risk factors.[9]

While the incidence of CVD is higher in diabetic patients as compared to non-diabetics in all populations studied, there exists clear geographic and ethnic differences in the relative risk of CVD among diabetic patients that cannot be entirely explained by differences in conventional cardiac risk factors between these groups.[10-20] For example, analysis of the relative risk of CVD in different ethnic groups living in the United Kingdom has shown that diabetic patients of South Asian origin have a markedly increased risk[12,15], while African-Carribean diabetic patients have a markedly decreased risk[14,16] of CVD as compared to diabetic patients of European origin.

These studies suggest that genetic differences could contribute to differences in susceptibility to CVD in the diabetic patient.

While conceiving the present invention it was hypothesized that a possibility is a functional allelic polymorphism in the haptoglobin gene.

Haptoglobin (Hp) is a hemoglobin-binding serum protein which plays a major role in the protection against heme-driven oxidative stress.[23,24] Mice lacking the Hp gene demonstrate a dramatic increase in oxidative stress and oxidative tissue damage particularly in the kidney. In man, there are two common alleles for Hp (1 and 2) manifesting as three major phenotypes 1-1, 2-1 and 2-2.[21-23]

Functional differences in the hemoglobin-binding capacity of the three phenotypes have been demonstrated. Hp in patients with the Hp 1-1 phenotype is able to bind more hemoglobin on per gram basis than Hps containing products of the haptoglobin 2 allele.[23] Haptoglobin molecules in patients with the haptoglobin 1-1 phenotype are also more efficient antioxidants, since the smaller size of haptoglobin 1-1 facilitates its entry to extravascular sites of oxidative tissue injury compared to products of the haptoglobin 2 allele. This also includes a significantly greater glomerular sieving of haptoglobin in patients with haptoglobin 1-1.[22]

The haptoglobin 2 allele appears to have arisen from the 1 allele via a partial gene duplication event approximately 20 million years ago and to have spread in the world population as a result of selective pressures related to resistance to infectious agents.[24,25] Presently the haptoglobin alleles differ dramatically in their relative frequency among different ethnic groups.[26] The gene duplication event has resulted in a dramatic change in the biophysical and biochemical properties of the haptoglobin protein encoded by each of the 2 alleles. For example, the protein product of the 1 allele appears to be a superior antioxidant compared to that produced by the 2 allele.[23] The haptoglobin phenotype of any individual, 1-1, 2-1 or 2-2, is readily determined from 10 microliters of plasma by gel electrophoresis.

It was recently demonstrated that the haptoglobin phenotype is predictive of the development of a number of microvascular complications in the diabetic patient.[27-29] Specifically, it was shown that patients who are homozygous for the haptoglobin 1 allele are at decreased risk for developing retinopathy and nephropathy. This effect, at least for nephropathy, has been observed in both type 1 and type 2 diabetic patients and the relevance strengthened by the finding of a gradient effect with respect to the number of haptoglobin 2 alleles and the development of nephropathy.[29] Furthermore, it was shown that the haptoglobin phenotype may be predictive of the development of macrovascular complications in the diabetic patient. We have shown that the development of restenosis after percutaneous coronary angioplasty is significantly decreased in diabetic patients with the 1-1 haptoglobin phenotype.[27,30] Previous retrospective and cross-sectional studies examining haptoglobin phenotype and coronary artery disease in the general population have yielded conflicting results.[31-38] The role of haptoglobin phenotype in the development of atherosclerotic coronary artery disease in the diabetic state has not been studied.

American Indians, previously thought to be resistant to developing coronary artery disease, are presently experiencing CVD in epidemic proportions.[20] This increased incidence of CVD has been attributed to the sharp increase in type 2 diabetes in this population.[1,2] The Strong Heart Study has examined the incidence, prevalence and risk factors of cardiovascular disease in American Indian populations in three geographic areas since 1988 with continued surveillance to the present.[20] The relative genetic homogeneity of this population of patients may permit identification of specific genetic factors that contribute to CVD disease in the diabetic state.

Accordingly, while reducing the present invention to practice, an attempt was made to determine the relative risk of CVD in diabetic patients according to haptoglobin phenotype in a case/control sample from the Strong Heart Study.

WO98/37419 teaches a method and kit for determining a haptoglobin phenotype and specifically relates to applications involving human haptoglobin. Teachings of this application focus on use of the haptoglobin 2-2 phenotype as an independent risk factor, specifically in relation to target organ damage in refractory essential hypertension, in relation to atherosclerosis (in the general population) and acute myocardial infarction and in relation to mortality from HIV infection. This application does not teach the use of haptoglobin phenotype as a risk factor in cardiovascular disease in DM. Because of the tendency of a haptoglobin 2-2 phenotype to make patients more prone to oxidative stress, it might be argued that use of a 2-2 phenotype as a negative predictor for cardiovascular disease in DM is indirectly implied by this patent. However, teachings of this patent do not include the idea that haptoglobin 1-1 phenotype is a positive predictor for reduced tendency towards cardiovascular disease in DM. Teachings of PCT WO98/37419 include use of a haptoglobin binding partner.

In other words, it is known that oxidative stress originating from Hp 2-1 or 2-2 phenotype leads to vascular complications in the general populations. It is also known that certain vascular complications are associated with oxidative stress associated with DM. It is, therefore plausible to assume the oxidative stress originating from either Hp 2-1 or 2-2 phenotype combined with that originating from DM will result in diabetes associated vascular complications. At present, it is, however, not known and cannot be predicted whether Hp1-1 phenotype mitigates the vascular complications in diabetic patients. This is the case, because DM and Hp1-1 phenotypes have opposing effects on the level of oxidative stress.

The binding partner according to PCT WO98/37419 may be any molecule with at least two locations by which it binds haptoglobin. The locations may be formed by a peptide, antibody, or a portion thereof, or by a lectin, a cell receptor, a molecular imprint or a bacterial antigen or a portion thereof. Teachings of this patent focus specifically on the use of the T4 antigen of S. pyogenes. All haptoglobins contain both alpha chains and beta chains. Beta chains are identical in all haptoglobins, while alpha chains differ between the two alleles of the haptoglobin gene. The alpha 2 chain of haptoglobin is the result of a mutation based on an unequal crossing over and includes 142 amino acids, in contrast to the 83 amino acids of the alpha 1 chain. Immunologically the alpha 1 and alpha 2 chains are similar, with the exception of a unique sequence of amino acid residues in the alpha 2 chain (Ala-Val-Gly-Asp-Lys-Leu-Pro-Glu-Cys-Glu-Ala-Asp-Asp-Gly-Gln-Pro-Pro-Pro-Lys-Cys-Ile, SEQ ID NO: 1). Any portion of this unique peptide sequence is therefore a suitable epitope for raising antibodies to differentiate between haptoglobins containing alpha 1 and alpha 2 chains as described in "Using Antibodies: A Laboratory Manual" (Ed Harlow and David Lane eds., Cold Spring Harbor Laboratory Press (1999)) which is fully incorporated herein by reference. Such antibodies might be monoclonal, polyclonal, or any portion thereof and may be enriched or purified by any one of a number of techniques known to those skilled in the art. In addition, the nucleotide sequence encoding this sequence can be readily employed to differentiate among Hp genotypes.

There is a widely recognized need for, and it would be highly advantageous to have a method to predict which specific DM patients have lower risk with respect to cardiovascular disease. Such a method would allow medical practitioners to make best use of available resources while minimizing risk to each patient to the greatest possible extent.

SUMMARY OF THE INVENTION

According to the present invention there is provided a method of evaluating a risk of a diabetic patient to develop cardiovascular disease (CVD). The method comprises determining a haptoglobin phenotype of the diabetic patient and thereby evaluating the risk of the diabetic patient to develop the cardiovascular disease (CVD), wherein the risk is decreased in diabetic patients with haptoglobin 1-1 phenotype as compared to patients with haptoglobin 1-2 or haptoglobin 2-2 phenotypes.

According to further features in preferred embodiments of the invention described below, the risk is also decreased in diabetic patients with haptoglobin 1-2 phenotype as compared to patients with haptoglobin 2-2 phenotype.

According to the present invention there is provided a kit for evaluating a risk of a diabetic patient to develop cardiovascular disease (CVD). The kit comprises packaged reagents for determining a haptoglobin phenotype of the diabetic patient and the kit is identified for use in evaluating a risk of a diabetic patient to develop cardiovascular disease (CVD).

According to further features in preferred embodiments of the invention described below, the step of determining the haptoglobin phenotype comprises determining a haptoglobin genotype of the diabetic patient.

According to still further features in the described preferred embodiments the step of determining the haptoglobin genotype of the diabetic patient comprises a method selected from the group consisting of a signal amplification method, a direct detection method and detection of at least one sequence change.

According to still further features in the described preferred embodiments the signal amplification method amplifies a molecule selected from the group consisting of a DNA molecule and an RNA molecule.

According to still further features in the described preferred embodiments the signal amplification method is selected from the group consisting of PCR, LCR (LAR), Self-Sustained Synthetic Reaction (3SR/NASBA) and Q-Beta (Qβ) Replicase reaction.

According to still further features in the described preferred embodiments the direct detection method is selected from the group consisting of a cycling probe reaction (CPR) and a branched DNA analysis.

According to still further features in the described preferred embodiments the detection of at least one sequence change employs a method selected from the group consisting of restriction fragment length polymorphism (RFLP analysis), allele specific oligonucleotide (ASO) analysis, Denaturing/Temperature Gradient Gel Electrophoresis (DGGE/TGGE), Single-Strand Conformation Polymorphism (SSCP) analysis and Dideoxy fingerprinting (ddF).

According to still further features in the described preferred embodiments the step of determining the haptoglobin phenotype comprises directly determining the haptoglobin phenotype of the diabetic patient.

According to still further features in the described preferred embodiments the step of determining the haptoglobin phenotype is effected by an immunological detection method.

According to still further features in the described preferred embodiments the immunological detection method is selected from the group consisting of a radio-immunoassay (RIA), an enzyme linked immunosorbent assay (ELISA), a western blot, an immunohistochemical analysis, and fluorescence activated cell sorting (FACS).

The present invention successfully addresses the shortcomings of the presently known configurations by providing a method for assessing the risk of hyperglycemic patients to develop cardiovascular disease, so as to allow for preventive medicine to be practiced where applicable.

DESCRIPTION OF THE PREFERRED EMBODIMENTS

The present invention is of a method of assessing the risk of hyperglycemic patients to develop cardiovascular disease, so as to allow for preventive medicine to be practiced where applicable.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The present invention is embodied by a method of evaluating a risk of a diabetic patient to develop cardiovascular disease (CVD). The method comprises determining a haptoglobin phenotype of the diabetic patient and thereby evaluating the risk of the diabetic patient to develop the cardiovascular disease (CVD), wherein the risk is decreased in diabetic patients with haptoglobin 1-1 phenotype as compared to patients with haptoglobin 1-2 or haptoglobin 2-2 phenotypes. Herein, it is unequivocally shown also that the risk is also decreased in diabetic patients with haptoglobin 1-2 phenotype as compared to patients with haptoglobin 2-2 phenotype.

The present invention also provides a kit for evaluating a risk of a diabetic patient to develop cardiovascular disease (CVD). The kit comprises packaged reagents for determining a haptoglobin phenotype of the diabetic patient and the kit is identified for use in evaluating a risk of a diabetic patient to develop cardiovascular disease (CVD). The nature of these reagents will become apparent to those of skill in the art from the following descriptions and further from well known and characterized sequence data of the haptoglobin 1 and 2 alleles.

The utility of the method and kit of the invention is demonstrated by data presented in Tables 1–3 of the Examples section that follows.

Thus, it is demonstrated herein, in a sample from a population-based longitudinal study, that the haptoglobin phenotype is a significant predictor of the development of CVD in individuals with diabetes even after adjustment for known CVD risk factors.

This hypothesis is further supported by the correlation between the frequency of the haptoglobin 1 allele in different ethnic groups and the relative incidence of diabetic microvascular and macrovascular complications in these groups.

For example, African-Carribeans with diabetes have a low relative risk of CVD[14,16] and microvascular complications and have a high frequency of the haptoglobin 1 allele (as high as 0.87 in some populations)[26] while diabetic Australian-Aborigines[19] and South Asian[12,15] peoples with diabetes have a high relative risk of CVD and diabetic microvascular[47] complications and a relatively low frequency of the haptoglobin 1 allele (0.18 and 0.09, respectively).[26]

Two mechanisms by which haptoglobin phenotype may influence the clinical course of atherosclerotic CVD were recently identified. First, a graded risk of restenosis after percutaneous transluminal coronary artery angioplasty was demonstrated to be related to the number of haptoglobin 2 alleles.[27,30] Second, it was demonstrated that diabetic individuals with the haptoglobin 2-1 phenotype are significantly more likely to have coronary artery collaterals as compared to individuals with the haptoglobin 2-2 phenotype with a similar degree of coronary artery disease. Inter-individual differences in the extent of the coronary collateral circulation have previously been demonstrated to be a key determinant of the size of a myocardial infarction.[48]

Several functions have been assigned to the haptoglobin protein that may impact on the development of atherosclerosis. It has been appreciated for over 60 years that a major function of serum haptoglobin is to bind free hemoglobin.[22] This interaction is thought to help scavenge iron and prevent its loss in the urine and to serve as an antioxidant thereby protecting tissues against hemoglobin mediated tissue oxidation.[23] The antioxidant capacity of the different haptoglobin phenotypes has been shown to differ with the haptoglobin 1-1 protein appearing to confer superior antioxidant protection as compared to the other forms of the protein.[23] Such an antioxidant hypothesis is particularly intriguing given the apparent important role of oxidative stress in the development of diabetic vascular complications.[49,50] Perhaps further amplifying apparent differences in the oxidative protection afforded by the different types of haptoglobin are gross differences in size of the haptoglobin protein present in individuals with the different phenotypes. Haptoglobin 1-1 is markedly smaller then haptoglobin 2-2 and thus may be better able to sieve into the extravascular compartment and prevent hemoglobin mediated tissue damage at sites of vascular injury.[23]

Haptoglobin has also been demonstrated to play a role as an immunomodulator that may not be unrelated to its role in hemoglobin metabolism.[21,23] A specific receptor for the haptoglobin-hemoglobin complex has recently been definitively identified on monocyte/macrophages as CD16351, a member of the group B scavenger receptor cysteine-rich superfamily.[52] Another member of this superfamily of scavenger receptors, CD36, has previously been shown to play an important role in LDL metabolism with profound significance for the development of atherosclerotic lesions.[53–55] Haptoglobin 2-2 complexed to hemoglobin was found to have a 10 fold higher affinity for this receptor than haptoglobin 1-1 complexed to hemoglobin.[51] Ligand binding to CD163 has been shown to induce a tyrosine-kinase dependent signal cascade resulting in secretion of a number of inflammatory cytokines.[56] Haptoglobin alone has also been demonstrated to bind to granulocytes and monocytes. Haptoglobin appears to block the neutrophil response to a variety of agonists with defined plasma membrane receptors suggesting that it may serve as an antagonist for receptor-ligand interaction of the immune system.[57] Specific binding of haptoglobin has been demonstrated to the MAC-1 or CD11b/CD18 receptor[58], a member of the integrin family. These integrins have been shown to play a major role in the response of the vessel wall to injury.[59]

An important role of bacterial infection in the development and destabilization of the atherosclerotic plaque has recently been suggested by many investigations.[60] In this regard it may be of importance vis a vis the differential risk of atherosclerosis associated with haptoglobin phenotype that the phenotypes appear to differ in their ability to prevent bacterial and viral replication in vitro and in vitro.[23–25] This may be due to differences in iron scavenging[23] as well as to differences in immunoregulation afforded by the different phenotypes.[51]

These findings are in complete agreement with our findings regarding the haptoglobin phenotype and the development of diabetic microvascular complications. The marked differences in the relative risk of patients with the different haptoglobin phenotypes would appear to warrant wide scale testing of diabetic patients to be used in CVD risk stratification algorithms and in evaluation of potential therapeutic interventions designed to prevent CVD in the diabetic patient.

According to various preferred embodiments of the method of the present invention, determining the haptoglobin phenotype of a testee is effected by any one of a variety of methods including, but not limited to, a signal amplification method, a direct detection method and detection of at least one sequence change. These methods determine a phenotype indirectly, by determining a genotype. As will be explained hereinbelow, determination of a haptoglobin phenotype may also be accomplished directly by analysis of haptoglobin gene products.

The signal amplification method according to various preferred embodiments of the present invention may amplify, for example, a DNA molecule or an RNA molecule. Signal amplification methods which might be used as part of the present invention include, but are not limited to PCR, LCR (LAR), Self-Sustained Synthetic Reaction (3SR/NASBA) or a Q-Beta (Qβ) Replicase reaction.

Polymerase Chain Reaction (PCR): The polymerase chain reaction (PCR), as described in U.S. Pat. Nos. 4,683,195 and 4,683,202 to Mullis and Mullis et al., is a method of increasing the concentration of a segment of target sequence in a mixture of genomic DNA without cloning or purification. This technology provides one approach to the problems of low target sequence concentration. PCR can be used to directly increase the concentration of the target to an easily detectable level. This process for amplifying the target sequence involves the introduction of a molar excess of two oligonucleotide primers which are complementary to their respective strands of the double-stranded target sequence to the DNA mixture containing the desired target sequence. The mixture is denatured and then allowed to hybridize. Following hybridization, the primers are extended with polymerase so as to form complementary strands. The steps of denaturation, hybridization (annealing), and polymerase extension (elongation) can be repeated as often as needed, in order to obtain relatively high concentrations of a segment of the desired target sequence.

The length of the segment of the desired target sequence is determined by the relative positions of the primers with respect to each other, and, therefore, this length is a controllable parameter. Because the desired segments of the target sequence become the dominant sequences (in terms of concentration) in the mixture, they are said to be "PCR-amplified."

Ligase Chain Reaction (LCR or LAR): The ligase chain reaction [LCR; sometimes referred to as "Ligase Amplification Reaction" (LAR)] described by Barany, Proc. Natl. Acad. Sci., 88:189 (1991); Barany, PCR Methods and Applic., 1:5 (1991); and Wu and Wallace, Genomics 4:560 (1989) has developed into a well-recognized alternative method of amplifying nucleic acids. In LCR, four oligonucleotides, two adjacent oligonucleotides which uniquely hybridize to one strand of target DNA, and a complementary set of adjacent oligonucleotides, which hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, and ligation amplify a short segment of DNA. LCR has also been used in combination with PCR to achieve enhanced detection of single-base changes. Segev, PCT Publication No. WO9001069 A1 (1990). However, because the four oligonucleotides used in this assay can pair to form two short ligateable fragments, there is the potential for the generation of target-independent background signal. The use of LCR for mutant screening is limited to the examination of specific nucleic acid positions.

Self-Sustained Synthetic Reaction (3SR/NASBA): The self-sustained sequence replication reaction (3SR) (Guatelli et al., Proc. Natl. Acad. Sci., 87:1874–1878, 1990), with an erratum at Proc. Natl. Acad. Sci., 87:7797, 1990) is a transcription-based in vitro amplification system (Kwok et al., Proc. Natl. Acad. Sci., 86:1173–1177, 1989) that can exponentially amplify RNA sequences at a uniform temperature. The amplified RNA can then be utilized for mutation detection (Fahy et al., PCR Meth. Appl., 1:25–33, 1991). In this method, an oligonucleotide primer is used to add a phage RNA polymerase promoter to the 5' end of the sequence of interest. In a cocktail of enzymes and substrates that includes a second primer, reverse transcriptase, RNase H, RNA polymerase and ribo- and deoxyribonucleoside triphosphates, the target sequence undergoes repeated rounds of transcription, cDNA synthesis and second-strand synthesis to amplify the area of interest. The use of 3SR to detect mutations is kinetically limited to screening small segments of DNA (e.g., 200–300 base pairs).

Q-Beta (Qβ) Replicase: In this method, a probe which recognizes the sequence of interest is attached to the replicatable RNA template for Qβ replicase. A previously identified major problem with false positives resulting from the replication of unhybridized probes has been addressed through use of a sequence-specific ligation step. However, available thermostable DNA ligases are not effective on this RNA substrate, so the ligation must be performed by T4 DNA ligase at low temperatures (37 degrees C.). This prevents the use of high temperature as a means of achieving specificity as in the LCR, the ligation event can be used to detect a mutation at the junction site, but not elsewhere.

A successful diagnostic method must be very specific. A straight-forward method of controlling the specificity of nucleic acid hybridization is by controlling the temperature of the reaction. While the 3SR/NASBA, and Qβ systems are all able to generate a large quantity of signal, one or more of the enzymes involved in each cannot be used at high temperature (i.e., >55 degrees C.). Therefore the reaction temperatures cannot be raised to prevent non-specific hybridization of the probes. If probes are shortened in order to make them melt more easily at low temperatures, the likelihood of having more than one perfect match in a complex genome increases. For these reasons, PCR and LCR currently dominate the research field in detection technologies.

The basis of the amplification procedure in the PCR and LCR is the fact that the products of one cycle become usable templates in all subsequent cycles, consequently doubling the population with each cycle. The final yield of any such doubling system can be expressed as: $(1+X)^n=y$, where "X" is the mean efficiency (percent copied in each cycle), "n" is the number of cycles, and "y" is the overall efficiency, or yield of the reaction (Mullis, PCR Methods Applic., 1:1, 1991). If every copy of a target DNA is utilized as a template in every cycle of a polymerase chain reaction, then the mean efficiency is 100%. If 20 cycles of PCR are performed, then the yield will be $2^{20}$, or 1,048,576 copies of the starting material. If the reaction conditions reduce the mean efficiency to 85%, then the yield in those 20 cycles will be only $1.85^{20}$, or 220,513 copies of the starting material. In other words, a PCR running at 85% efficiency will yield only 21% as much final product, compared to a reaction running at 100% efficiency. A reaction that is reduced to 50% mean efficiency will yield less than 1% of the possible product.

In practice, routine polymerase chain reactions rarely achieve the theoretical maximum yield, and PCRs are usually run for more than 20 cycles to compensate for the lower yield. At 50% mean efficiency, it would take 34 cycles to achieve the million-fold amplification theoretically possible in 20, and at lower efficiencies, the number of cycles required becomes prohibitive. In addition, any background products that amplify with a better mean efficiency than the intended target will become the dominant products.

Also, many variables can influence the mean efficiency of PCR, including target DNA length and secondary structure, primer length and design, primer and dNTP concentrations, and buffer composition, to name but a few. Contamination of the reaction with exogenous DNA (e.g., DNA spilled onto lab surfaces) or cross-contamination is also a major consideration. Reaction conditions must be carefully optimized for each different primer pair and target sequence, and the process can take days, even for an experienced investigator. The laboriousness of this process, including numerous technical considerations and other factors, presents a significant drawback to using PCR in the clinical setting. Indeed, PCR has yet to penetrate the clinical market in a significant way. The same concerns arise with LCR, as LCR must also be optimized to use different oligonucleotide sequences for each target sequence. In addition, both methods require expensive equipment, capable of precise temperature cycling.

Many applications of nucleic acid detection technologies, such as in studies of allelic variation, involve not only detection of a specific sequence in a complex background, but also the discrimination between sequences with few, or single, nucleotide differences. One method of the detection of allele-specific variants by PCR is based upon the fact that it is difficult for Taq polymerase to synthesize a DNA strand when there is a mismatch between the template strand and the 3' end of the primer. An allele-specific variant may be detected by the use of a primer that is perfectly matched with only one of the possible alleles; the mismatch to the other allele acts to prevent the extension of the primer, thereby preventing the amplification of that sequence. This method has a substantial limitation in that the base composition of the mismatch influences the ability to prevent extension across the mismatch, and certain mismatches do not prevent extension or have only a minimal effect (Kwok et al., Nucl. Acids Res., 18:999, 1990)

A similar 3'-mismatch strategy is used with greater effect to prevent ligation in the LCR (Barany, PCR Meth. Applic., 1:5, 1991). Any mismatch effectively blocks the action of the thermostable ligase, but LCR still has the drawback of target-independent background ligation products initiating the amplification. Moreover, the combination of PCR with subsequent LCR to identify the nucleotides at individual positions is also a clearly cumbersome proposition for the clinical laboratory.

The direct detection method according to various preferred embodiments of the present invention may be, for example a cycling probe reaction (CPR) or a branched DNA analysis.

When a sufficient amount of a nucleic acid to be detected is available, there are advantages to detecting that sequence directly, instead of making more copies of that target, (e.g., as in PCR and LCR). Most notably, a method that does not amplify the signal exponentially is more amenable to quantitative analysis. Even if the signal is enhanced by attaching multiple dyes to a single oligonucleotide, the correlation between the final signal intensity and amount of target is direct. Such a system has an additional advantage that the products of the reaction will not themselves promote further reaction, so contamination of lab surfaces by the products is not as much of a concern. Traditional methods of direct detection including Northern and Southern band RNase protection assays usually require the use of radioactivity and are not amenable to automation. Recently devised techniques have sought to eliminate the use of radioactivity and/or improve the sensitivity in automateable formats. Two examples are the "Cycling Probe Reaction" (CPR), and "Branched DNA" (bDNA).

Cycling probe reaction (CPR): The cycling probe reaction (CPR) (Duck et al., BioTech., 9:142, 1990), uses a long chimeric oligonucleotide in which a central portion is made of RNA while the two termini are made of DNA. Hybridization of the probe to a target DNA and exposure to a thermostable RNase H causes the RNA portion to be digested. This destabilizes the remaining DNA portions of the duplex, releasing the remainder of the probe from the target DNA and allowing another probe molecule to repeat the process. The signal, in the form of cleaved probe molecules, accumulates at a linear rate. While the repeating process increases the signal, the RNA portion of the oligonucleotide is vulnerable to RNases that may carried through sample preparation.

Branched DNA: Branched DNA (bDNA), described by Urdea et al., Gene 61:253–264 (1987), involves oligonucleotides with branched structures that allow each individual oligonucleotide to carry 35 to 40 labels (e.g., alkaline phosphatase enzymes). While this enhances the signal from a hybridization event, signal from non-specific binding is similarly increased.

The detection of at least one sequence change according to various preferred embodiments of the present invention may be accomplished by, for example restriction fragment length polymorphism (RFLP analysis), allele specific oligonucleotide (ASO) analysis, Denaturing/Temperature Gradient Gel Electrophoresis (DGGE/TGGE), Single-Strand Conformation Polymorphism (SSCP) analysis or Dideoxy fingerprinting (ddF).

The demand for tests which allow the detection of specific nucleic acid sequences and sequence changes is growing rapidly in clinical diagnostics. As nucleic acid sequence data for genes from humans and pathogenic organisms accumulates, the demand for fast, cost-effective, and easy-to-use tests for as yet mutations within specific sequences is rapidly increasing.

A handful of methods have been devised to scan nucleic acid segments for mutations. One option is to determine the entire gene sequence of each test sample (e.g., a bacterial isolate). For sequences under approximately 600 nucleotides, this may be accomplished using amplified material (e.g., PCR reaction products). This avoids the time and expense associated with cloning the segment of interest. However, specialized equipment and highly trained personnel are required, and the method is too labor-intense and expensive to be practical and effective in the clinical setting.

In view of the difficulties associated with sequencing, a given segment of nucleic acid may be characterized on several other levels. At the lowest resolution, the size of the molecule can be determined by electrophoresis by comparison to a known standard run on the same gel. A more detailed picture of the molecule may be achieved by cleavage with combinations of restriction enzymes prior to electrophoresis, to allow construction of an ordered map. The presence of specific sequences within the fragment can be detected by hybridization of a labeled probe, or the precise nucleotide sequence can be determined by partial chemical degradation or by primer extension in the presence of chain-terminating nucleotide analogs.

Restriction fragment length polymorphism (RFLP): For detection of single-base differences between like sequences, the requirements of the analysis are often at the highest level of resolution. For cases in which the position of the nucleotide in question is known in advance, several methods have been developed for examining single base changes without direct sequencing. For example, if a mutation of interest happens to fall within a restriction recognition sequence, a change in the pattern of digestion can be used as a diagnostic tool (e.g., restriction fragment length polymorphism [RFLP] analysis).

Single point mutations have been also detected by the creation or destruction of RFLPs. Mutations are detected and localized by the presence and size of the RNA fragments generated by cleavage at the mismatches. Single nucleotide mismatches in DNA heteroduplexes are also recognized and cleaved by some chemicals, providing an alternative strategy to detect single base substitutions, generically named the "Mismatch Chemical Cleavage" (MCC) (Gogos et al., Nucl. Acids Res., 18:6807–6817, 1990). However, this method requires the use of osmium tetroxide and piperidine, two highly noxious chemicals which are not suited for use in a clinical laboratory.

RFLP analysis suffers from low sensitivity and requires a large amount of sample. When RFLP analysis is used for the detection of point mutations, it is, by its nature, limited to the detection of only those single base changes which fall within a restriction sequence of a known restriction endonuclease. Moreover, the majority of the available enzymes have 4 to 6 base-pair recognition sequences, and cleave too frequently for many large-scale DNA manipulations (Eckstein and Lilley (eds.), Nucleic Acids and Molecular Biology, vol. 2, Springer-Verlag, Heidelberg, 1988). Thus, it is applicable only in a small fraction of cases, as most mutations do not fall within such sites.

A handful of rare-cutting restriction enzymes with 8 base-pair specificities have been isolated and these are widely used in genetic mapping, but these enzymes are few in number, are limited to the recognition of G+C-rich sequences, and cleave at sites that tend to be highly clustered (Barlow and Lehrach, Trends Genet., 3:167, 1987). Recently, endonucleases encoded by group I introns have been discovered that might have greater than 12 base-pair specificity (Perlman and Butow, Science 246:1106, 1989), but again, these are few in number.

Allele specific oligonucleotide (ASO): If the change is not in a recognition sequence, then allele-specific oligonucleotides (ASOs), can be designed to hybridize in proximity to the mutated nucleotide, such that a primer extension or ligation event can bused as the indicator of a match or a mis-match. Hybridization with radioactively labeled allelic specific oligonucleotides (ASO) also has been applied to the detection of specific point mutations (Conner et al., Proc. Natl. Acad. Sci., 80:278–282, 1983). The method is based on the differences in the melting temperature of short DNA fragments differing by a single nucleotide. Stringent hybridization and washing conditions can differentiate between mutant and wild-type alleles. The ASO approach applied to PCR products also has been extensively utilized by various researchers to detect and characterize point mutations in ras genes (Vogelstein et al., N. Eng. J. Med., 319:525–532, 1988; and Farr et al., Proc. Natl. Acad. Sci., 85:1629–1633, 1988), and gsp/gip oncogenes (Lyons et al., Science 249:655–659, 1990). Because of the presence of various nucleotide changes in multiple positions, the ASO method requires the use of many oligonucleotides to cover all possible oncogenic mutations.

With either of the techniques described above (i.e., RFLP and ASO), the precise location of the suspected mutation must be known in advance of the test. That is to say, they are inapplicable when one needs to detect the presence of a mutation within a gene or sequence of interest.

Denaturing/Temperature Gradient Gel Electrophoresis (DGGE/TGGE): Two other methods rely on detecting changes in electrophoretic mobility in response to minor sequence changes. One of these methods, termed "Denaturing Gradient Gel Electrophoresis" (DGGE) is based on the observation that slightly different sequences will display different patterns of local melting when electrophoretically resolved on a gradient gel. In this manner, variants can be distinguished, as differences in melting properties of homoduplexes versus heteroduplexes differing in a single nucleotide can detect the presence of mutations in the target sequences because of the corresponding changes in their electrophoretic mobilities. The fragments to be analyzed, usually PCR products, are "clamped" at one end by a long stretch of G-C base pairs (30–80) to allow complete denaturation of the sequence of interest without complete dissociation of the strands. The attachment of a GC "clamp" to the DNA fragments increases the fraction of mutations that can be recognized by DGGE (Abrams et al., Genomics 7:463–475, 1990). Attaching a GC clamp to one primer is critical to ensure that the amplified sequence has a low dissociation temperature (Sheffield et al., Proc. Natl. Acad. Sci., 86:232–236, 1989; and Lerman and Silverstein, Meth. Enzymol., 155:482–501, 1987). Modifications of the technique have been developed, using temperature gradients (Wartell et al., Nucl. Acids Res., 18:2699–2701, 1990), and the method can be also applied to RNA:RNA duplexes (Smith et al., Genomics 3:217–223, 1988).

Limitations on the utility of DGGE include the requirement that the denaturing conditions must be optimized for each type of DNA to be tested. Furthermore, the method requires specialized equipment to prepare the gels and maintain the needed high temperatures during electrophoresis. The expense associated with the synthesis of the clamping tail on one oligonucleotide for each sequence to be tested is also a major consideration. In addition, long running times are required for DGGE. The long running time of DGGE was shortened in a modification of DGGE called constant denaturant gel electrophoresis (CDGE) (Borrensen et al., Proc. Natl. Acad. Sci. USA 88:8405, 1991). CDGE requires that gels be performed under different denaturant conditions in order to reach high efficiency for the detection of mutations.

A technique analogous to DGGE, termed temperature gradient gel electrophoresis (TGGE), uses a thermal gradient rather than a chemical denaturant gradient (Scholz, et al., Hum. Mol. Genet. 2:2155, 1993). TGGE requires the use of specialized equipment which can generate a temperature gradient perpendicularly oriented relative to the electrical field. TGGE can detect mutations in relatively small fragments of DNA therefore scanning of large gene segments requires the use of multiple PCR products prior to running the gel.

Single-Strand Conformation Polymorphism (SSCP): Another common method, called "Single-Strand Conformation Polymorphism" (SSCP) was developed by Hayashi, Sekya and colleagues (reviewed by Hayashi, PCR Meth. Appl., 1:34–38, 1991) and is based on the observation that single strands of nucleic acid can take on characteristic conformations in non-denaturing conditions, and these conformations influence electrophoretic mobility. The complementary strands assume sufficiently different structures that one strand may be resolved from the other. Changes in sequences within the fragment will also change the conformation, consequently altering the mobility and allowing this to be used as an assay for sequence variations (Orita, et al., Genomics 5:874–879, 1989).

The SSCP process involves denaturing a DNA segment (e.g., a PCR product) that is labeled on both strands, followed by slow electrophoretic separation on a nondenaturing polyacrylamide gel, so that intra-molecular interactions can form and not be disturbed during the run. This technique is extremely sensitive to variations in gel composition and temperature. A serious limitation of this method is the relative difficulty encountered in comparing data generated in different laboratories, under apparently similar conditions.

Dideoxy fingerprinting (ddF): The dideoxy fingerprinting (ddF) is another technique developed to scan genes for the presence of mutations (Liu and Sommer, PCR Methods Appli., 4:97, 1994). The ddF technique combines components of Sanger dideoxy sequencing with SSCP. A dideoxy sequencing reaction is performed using one dideoxy terminator and then the reaction products are electrophoresed on nondenaturing polyacrylamide gels to detect alterations in mobility of the termination segments as in SSCP analysis. While ddF is an improvement over SSCP in terms of increased sensitivity, ddF requires the use of expensive dideoxynucleotides and this technique is still limited to the analysis of fragments of the size suitable for SSCP (i.e., fragments of 200–300 bases for optimal detection of mutations).

In addition to the above limitations, all of these methods are limited as to the size of the nucleic acid fragment that can be analyzed. For the direct sequencing approach, sequences of greater than 600 base pairs require cloning, with the consequent delays and expense of either deletion subcloning or primer walking, in order to cover the entire fragment. SSCP and DGGE have even more severe size limitations. Because of reduced sensitivity to sequence changes, these methods are not considered suitable for larger fragments. Although SSCP is reportedly able to detect 90% of single-base substitutions within a 200 base-pair fragment, the detection drops to less than 50% for 400 base pair fragments. Similarly, the sensitivity of DGGE decreases as the length of the fragment reaches 500 base-pairs. The ddF technique, as a combination of direct sequencing and SSCP, is also limited by the relatively small size of the DNA that can be screened.

According to a presently preferred embodiment of the present invention the step of searching for the mutation or mutations in any of the genes listed above, such as, for example, the reduced folate carrier (RFC) gene, in tumor cells or in cells derived from a cancer patient is effected by a single strand conformational polymorphism (SSCP) technique, such as cDNA-SSCP or genomic DNA-SSCP. However, alternative methods can be employed, including, but not limited to, nucleic acid sequencing, polymerase chain reaction, ligase chain reaction, self-sustained synthetic reaction, Qβ-Replicase, cycling probe reaction, branched DNA, restriction fragment length polymorphism analysis, mismatch chemical cleavage, heteroduplex analysis, allele-specific oligonucleotides, denaturing gradient gel electrophoresis, constant denaturant gel electrophoresis, temperature gradient gel electrophoresis and dideoxy fingerprinting.

Determination of a haptoglobin phenotype may, as if further exemplified in the Examples section that follows, also be accomplished directly, by analyzing the protein gene products of the haptoglobin gene, or portions thereof. Such a direct analysis is often accomplished using an immunological detection method.

Immunological detection methods are fully explained in, for example, "Using Antibodies: A Laboratory Manual" (Ed Harlow, David Lane eds., Cold Spring Harbor Laboratory Press (1999)) and those familiar with the art will be capable of implementing the various techniques summarized hereinbelow as part of the present invention. All of the immunological techniques require antibodies specific to at least one of the two haptoglobin alleles. Immunological detection methods suited for use as part of the present invention include, but are not limited to, radio-immunoassay (RIA), enzyme linked immunosorbent assay (ELISA), western blot, immunohistochemical analysis, and fluorescence activated cell sorting (FACS).

Radio-immunoassay (RIA): In one version, this method involves precipitation of the desired substrate, haptoglobin in this case and in the methods detailed hereinbelow, with a specific antibody and radiolabelled antibody binding protein (e.g., protein A labeled with $I^{125}$) immobilized on a precipitable carrier such as agarose beads. The number of counts in the precipitated pellet is proportional to the amount of substrate.

In an alternate version of the RIA, A labeled substrate and an unlabelled antibody binding protein are employed. A sample containing an unknown amount of substrate is added in varying amounts. The decrease in precipitated counts from the labeled substrate is proportional to the amount of substrate in the added sample.

Enzyme linked immunosorbent assay (ELISA): This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a calorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabelled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Immunohistochemical analysis: This method involves detection of a substrate in situ in fixed cells by substrate specific antibodies. The substrate specific antibodies may be enzyme linked or linked to fluorophores. Detection is by microscopy and subjective evaluation. If enzyme linked antibodies are employed, a calorimetric reaction may be required.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

It will be appreciated by one ordinarily skilled in the art that determining the haptoglobin phenotype of an individual, either directly or genetically, may be effected using any suitable biological sample derived from the examined individual, including, but not limited to, blood, plasma, blood cells, saliva or cells derived by mouth wash, and body secretions such as urine and tears, and from biopsies, etc.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I–III Cellis, J. E., ed. (1994); "Culture of Animal Cells—A Manual of Basic Technique" by Freshney, Wiley-Liss, N.Y. (1994), Third Edition; "Current Protocols in Immunology" Volumes I–III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

EXPERIMENTAL METHODS

Before presenting examples which provide experimental data to support the present invention, reference is made to the following methods:

Patients:

Detailed descriptions of the Strong Heart Study study design, survey methods and laboratory techniques and the participating Indian communities have been previously published.[20,39,40]

The study cohort consists of over 4,549 individuals aged 45 to 74 who were seen at the first examination conducted between July 1989 and January 1992. Participation rates of all eligible tribe members averaged 64%. Non-participants were similar to participants in age and self reported frequency of diabetes. Reexamination rates for those alive at the second examination (July 1993 to December 1995) averaged 88% and at the third examination (July 1997 to December 1999) averaged 90%.

The clinical examination at each phase consisted of a personal interview and a physical examination. Fasting blood samples were taken for biochemical measurements and a 75 grams oral glucose tolerance test was performed. Blood samples were collected in the presence of EDTA, the plasma was harvested and stored at −20° C. Standardized blood pressure measurements were obtained and electrocardiograms were recorded and coded as previously described.[39,40] Participants were classified as diabetic according to World Health Organization criteria.[41] Participants were considered hypertensive if they were taking anti-hypertensive medications or if they had a systolic blood pressure greater than 140 mm Hg or a diastolic blood pressure of greater than 90 mm Hg.

Deaths among the Strong Heart Study cohort between 1988 and the present were identified through tribal and hospital records and by direct contact by study personnel with participants and their families. Copies of death certificates were obtained from state health departments and ICD-9 coded centrally by a nosologist. Possible CVD deaths were initially identified from death certificates as described previously.[42] Cause of death was investigated through autopsy reports, medical records abstractions, and informant interviews as described previously.[42] All materials were reviewed independently by physician members of the Strong Heart Study Mortality Review Committee to confirm the cause of death. Criteria for fatal CVD and stroke were as described previously.[42]

Medical records were reviewed at each examination to identify any nonfatal cardiovascular events, definite MI and definite CVD as previously described[20,43], that had occurred since the previous examination. Records of those who did not participate in the second or third examination were also reviewed. For all potential CVD events or interventions, medical records were reviewed by trained medical record abstractors. Records of outpatient visits were reviewed and abstracted for procedures diagnostic of CVD (e.g., treadmill test, coronary angiography). Information obtained from chart review was reviewed by a physician member of the Strong Heart Study mortality or morbidity review committee to establish the specific CVD diagnosis. Blinded review of the abstracted records by other physician members of the Morbidity Review Committee showed >90% concordance in the diagnosis.

Definition of case and controls:

The present study is a case-control sample designed to examine the relationship between CVD and haptoglobin phenotype. 206 CVD cases and controls (matched for age, gender and geographic area) were subjected to this analysis.

Haptoglobin phenotyping:

Haptoglobin phenotyping was determined from 10 μl of EDTA-plasma by gel electrophoresis and peroxidase staining using a modification[44,45] of the method originally described by Smithies[46] which used starch gel electrophoresis and peroxidase staining with benzidine. Patients' plasma was stored at −20° C. All chemicals were purchased from Sigma Israel (Rehovot, Israel). A 10% hemoglobin solution in water was prepared from heparinized blood by first washing the blood cells 5 times in phosphate buffered saline and then lysing the cells in 9 ml of sterile water per ml of pelleted cell volume. The cell lysate was centrifuged at 10,000 g for 40 minutes and the supernatant containing hemoglobin was aliquoted and stored at −70° C. Serum (10 μl) was mixed with 2 μl of the 10% hemoglobin solution and the samples permitted to stand for 5 minutes at room temperature in order to allow the haptoglobin-hemoglobin complex to form. An equal volume (12 μl) of sample buffer containing 125 mM Tris Base pH 6.8, 20% (w/v) glycerol and 0.001% (w/v) bromophenol blue was added to each sample prior to running on the gel. The haptoglobin hemoglobin complex was resolved by polyacrylamide gel electrophoresis using a buffer containing 25 mM Tris Base and 192 mM glycine. The stacking gel was 4% polyacrylamide (29:1 acrylamide/bis-acrylamide) in 125 mM Tris Base, pH 6.8 and the separating gel was 4.7% polyacrylamide (29:1 acylamide/bis-acrylamide) in 360 mM Tris Base, pH 8.8. Electrophoresis was performed at a constant voltage of 250 volts for 3 hours. After the electrophoresis was completed the haptoglobin-hemoglobin complexes were visualized by soaking the gel in freshly prepared staining solution in a glass tray. The staining solution (prepared by adding the reagents in the order listed) contained 5 ml of 0.2% (w/v) 3,3',5,5'-tetramethylbenzidine in methanol, 0.5 ml dimethylsulfoxide, 10 ml of 5% (v/v) glacial acetic acid, 1 ml of 1% (w/v) potassium ferricyanide and 150 μl of 30% (w/w) hydrogen peroxide. The bands corresponding to the haptoglobin-hemoglobin complex were readily visible within 15 minutes and were stable for over 48 hours. All gels were documented with photographs. The haptoglobin phenotype of all samples was determined at the laboratory without any knowledge concerning the patient.

Plasma samples were received by the laboratory for analysis and haptoglobin phenotyping was possible on all but six of these samples. For these six patients it is not clear if they represent patients who do not make any haptoglobin (Hp 0 phenotype)[22,23] or that the haptoglobin concentration is below the detection limit for the assay described.

Statistical analysis:

CVD risk factors of age, gender, LDL and HDL cholesterol, triglycerides, systolic BP, BMI, diabetes, smoking status, family history of CVD and recruitment center were compared between cases and controls as well as between the three haptoglobin phenotypes. In addition DM characteristics consisting of insulin, fasting glucose levels, HbA1c, DM duration and family history of DM were compared between cases and controls as well as between the three haptoglobin phenotypes. Univariate and multinomial logistic regression modeling was performed to determine if these CVD risk factors and DM characteristics were related to phenotype. The likelihood ratio was used to test parameters.

A conditional logistic regression model was run modeling the probability of having a CVD event for a diabetic patient by the three haptoglobin phenotypes adjusting for the CVD risk factors and the DM characteristics. The diabetes-phenotype interaction was coded using two indicator variables, one for patients with diabetes and another for patients without diabetes. Model fit was assessed by an analysis of residuals.

EXPERIMENTAL RESULTS

The clinical characteristics of the case control cohort according to CVD risk factors and DM characteristics is shown in Table 1 below.

TABLE 1

CVD Risk Factors by Case-Control Status

| CVD Risk Factors | | Controls | | | Cases | | |
|---|---|---|---|---|---|---|---|
| | | Mean | STD | | Mean | STD | |
| Age | | 59.16 | 8.01 | | 60.09 | 8.08 | |
| LDL Cholesterol | | 112.1 | 30.44 | | 123.0 | 40.47 | |
| | | Median | Min | Max | Median | Min | Max |
| DM duration | | | | | 6.00 | 0.00 | 41.00 |
| Systolic BP | | 124.0 | 81.00 | 210.0 | 131.0 | 88.00 | 205.0 |
| BMI | | 29.76 | 17.71 | 48.07 | 29.84 | 19.59 | 72.36 |
| HbA1c | | 4.00 | 4.00 | 13.10 | 7.20 | 4.00 | 15.50 |
| Fasting Glucose | | 118.5 | 77.00 | 365.0 | 148.0 | 57.00 | 354.0 |
| Insulin | | 15.99 | 2.20 | 144.7 | 18.45 | 1.50 | 314.5 |
| | | n | % | | n | % | |
| Female Gender | | 102 | 49.51 | | 102 | 49.51 | |
| Diabetes | | 93 | 45.15 | | 146 | 70.89 | |
| Current Smoker | | 136 | 66.0 | | 143 | 70.69 | |
| Family hx DM | | 131 | 63.5 | | 145 | 70.34 | |
| Family hx CVD | | 119 | 57.77 | | 148 | 71.84 | |
| Center | OK | 74 | 35.92 | | 74 | 35.92 | |
| | SD | 73 | 35.44 | | 73 | 35.44 | |
| | AZ | 59 | 28.64 | | 59 | 28.64 | |

Cases and controls were matched for age, gender and geographic area. These data are consistent with previous finding in this population that diabetes, LDL cholesterol, and hypertension are all independent predictors of CVD.[20]

Haptoglobin phenotyping of this cohort revealed a distribution of 25% 1-1, 44% 2-1 and 31% 2-2. The frequency of the 1 allele was 0.47 which is in good agreement with haptoglobin allelic frequency for this population that has been previously reported.[26] No significant difference was found between the different haptoglobin phenotypes for any of the CVD risk factors or DM characteristics as determined both by univariate analysis and by multinomial logit regression analysis modeling the probability of having a 1-1 phenotype.

Table 2 below provides the conditional logistic regression predicting the probability of a CVD event for each of the haptoglobin phenotypes in diabetic and non-diabetic individuals prior to and after adjustment for CVD risk factors and DM characteristics.

TABLE 2

Conditional logistic regression predicting the probability of a CVD event

| Variable | OR | 95% CI | p-value |
|---|---|---|---|
| Unadjusted | | | |
| DM and Hp 2-1 (vs DM and Hp 1-1) | 2.32 | (1.27–4.23) | 0.006 |
| DM and Hp 2-2 (vs DM and Hp 1-1) | 5.08 | (2.37–10.89) | <0.001 |
| DM and Hp 2-2 (vs DM and Hp 2-1) | 3.26 | (1.67–6.37) | <0.001 |
| No DM, Hp 2-1 (vs no DM, Hp 1-1) | 0.63 | (0.33–1.20) | 0.159 |
| No DM, Hp 2-2 (vs no DM, Hp 1-1) | 1.10 | (0.53–2.30) | 0.795 |
| No DM, Hp 2-2 (vs no DM, Hp 2-1) | 0.75 | (0.40–1.38) | 0.350 |
| Adjusted for DM characteristics only | | | |
| DM and Hp 2-1 (vs DM and Hp 1-1) | 1.86 | (0.93–3.69) | 0.078 |
| DM and Hp 2-2 (vs DM and Hp 1-1) | 3.90 | (1.68–9.09) | 0.002 |
| DM and Hp 2-2 (vs DM and Hp 2-1) | 2.10 | (1.00–4.40) | 0.049 |
| No DM, Hp 2-1 (vs no DM, Hp 1-1) | 1.40 | (0.48–4.09) | 0.542 |
| No DM, Hp 2-2 (vs no DM, Hp 1-1) | 2.31 | (0.76–7.05) | 0.141 |
| No DM, Hp 2-2 (vs no DM, Hp 2-1) | 1.65 | (0.73–3.75) | 0.228 |
| Adjusted for DM characteristics and CVD factors | | | |
| DM and Hp 2-1 (vs DM and Hp 1-1) | 1.85 | (0.86–3.96) | 0.116 |
| DM and Hp 2-2 (vs DM and Hp 1-1) | 4.70 | (1.86–11.88) | 0.001 |
| DM and Hp 2-2 (vs DM and Hp 2-1) | 2.55 | (1.14–5.67) | 0.022 |
| No DM, Hp 2-1 (vs no DM, Hp 1-1) | 1.70 | (0.53–5.49) | 0.373 |
| No DM, Hp 2-2 (vs no DM, Hp 1-1) | 2.97 | (0.90–9.77) | 0.073 |
| No DM, Hp 2-2 (vs no DM, Hp 2-1) | 1.75 | (0.71–4.29) | 0.225 |

These data show, after adjustment for all CVD risk factors and DM characteristics, that among Strong Heart Study participants with diabetes, those with a haptoglobin phenotype of 2-2 are 4.7 (1.86–11.88 OR 95% CI) times more likely to have had a CVD event than those with a 1-1 phenotype (p=0.001) and 2.5 (1..14–5.67 OR 95% CI) times more likely to have had a CVD event than those with a 2-1 phenotype (p=0.022). Moreover, patients with a haptoglobin phenotype of 2-1 were 1.8 (0.86–3.96 OR 95% CI) times more likely to have had a CVD event than those with the 1-1 phenotype although this was not statistically significant. Taken together, these data suggest the existence of a graded risk conferred by the number of haptoglobin 2 alleles on the development of CVD in diabetic individuals.

Finally, in patients without diabetes a trend was observed of borderline statistical significance showing that the non-diabetic patients with a haptoglobin phenotype of 2-2 are 3.0 (0.90–9.77 OR 95% CI) times more likely to have had a CVD event than those non-diabetics with a 1-1 phenotype (p=0.073).

Table 3 below summarizes these results:

TABLE 3

Conditional Logistic Regression predicting the probability of a CVD event adjusted for DM and CVD risk factors

| Risk Factors | OR (of CVD) | 95% CI Lower | 95% CI Upper | p-value |
|---|---|---|---|---|
| DM and Hp 2-1 (vs dm and Hp 1—1) | 1.85 | 0.86 | 3.96 | 0.116 |
| DM and Hp 2-2 (vs dm and Hp 1—1) | 4.70 | 1.86 | 11.88 | 0.001 |
| DM and Hp 2-2 (vs dm and Hp 2-1) | 2.55 | 1.14 | 5.67 | .022 |
| No DM, Hp 2-1 (vs no dm, Hp 1—1) | 1.70 | 0.53 | 5.49 | 0.373 |
| No DM, Hp 2-2 (vs no dm, Hp 1—1) | 2.97 | 0.90 | 9.77 | 0.073 |
| No DM, Hp 2-2 (vs no dm, Hp 2-1) | 1.75 | 0.71 | 4.29 | 0.225 |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

List of references:
1. Howard B V, Magee M F. Diabetes and Cardiovascular Disease. Curr Atheroscler Rep 2000; 2; 476–481.
2. Aronson D, Rayfield E J. Diabetes in Textbook of Cardiovascular Medicine. Topol E J ed. Philadelphia, Lippincott-Raven Publishers, 1998: 171–194.
3. Stamler J, Vaccaro O, Neaton J D, Wentworth D. Diabetes, other risk factors and 12-year cardiovascular mortality for men screened in the multiple risk factor intervention trial. Diab Care 1993; 16: 434–444.
4. Kannel W, McGee D. Diabetes and glucose tolerance as risk factors for cardiovascular disease. The Framingham Study. Diab Care 1979; 2: 120–126.
5. Jarrett R J, Shipley M J. Type 2 (non-insulin dependent) diabetes mellitus and cardiovascular disease-putative association via common antecedents: Further evidence from the Whitehall Study. Diabetologia 1988; 31: 737–740.
6. Fontbonne A, Eschwege E, Cambien F, et al. Hypertryglyceridemia as a risk factor for coronary artery disease mortality in subjects with impaired glucose tolerance or diabetes: Results from the 11-year follow up of the Paris Prospective Study. Diabetologia 1989; 32: 300–304.
7. Donahue R P, Orchard T G. Diabetes mellitus and macrovascular complications. An epidemiological perspective. Diab Care 1992; 15: 1141–1155.
8. Barret-Connor E, Cohn B, Wingard D, Edelstein S L. Why is diabetes mellitus a stronger risk factor for fatal ischemic heart disease in women then in men? The Rancho Bernardo Study. JAMA 1991; 265: 627–631.
9. Hammoud T, Tanguay J F, Bourassa M G. Management of coronary artery disease: therapeutic options in patients with diabetes. J Am Coll Card 2000; 36: 355–365.

10. Head J, Fuller J H. International variations in mortality among diabetic patients. The WHO Multinational Study of Vascular Disease in Diabetics. Diabetologia 1990; 33: 447–481.
11. Grimaldi A, Heurtier A. Epidemiology of cardiovascular complications of diabetes. Diab Metab 1999; 3: 12–20.
12. Woods K L, Samanta A, Burden A C. Diabetes mellitus as a risk factor for acute myocardial infarction in Asians and Europeans. Br Ht J 1989; 62: 118–122.
13. Cruickshank J K, Alleyne S A. Black West Indian and matched white diabetics in Britain compared with diabetics in Jamaica: body mass, blood pressure and vascular disease. Diab Care 1987; 10: 170–179.
14. UK Prospective Diabetes Study Group. Ethnicity and cardiovascular disease. The incidence of myocardial infarction in white, south Asian and afro-Caribbean patients with type 2 diabetes. Diab Care 1998; 21: 1271–1277.
15. Mather H M, Chaturvedi N, Fuller J H. Mortality and morbidity from diabetes in south Asians and Europeans: 11-year follow up of the southall diabetes survey, London, UK. Diab Med 1998; 15: 53–59.
16. Chaturverdi N, Jarrett J, Morrish N, Keen H, Fuller J H. Differences in mortality and morbidity in African-carribean and European people with non-insulin dependent diabetes mellitus: results of 20 year follow up of a London cohort of a multinational study. Brit Med J 1996; 313: 848–852.
17. Chaturverdi N, Fuller J H. Ethnic differences in mortality from cardiovascular disease in the UK: do they persist in people with diabetes? J Epid Comm Health 1996; 50: 137–139.
18. Samanta A, Burden A C, Jagger C. A comparison of the clinical features and vascular complications of diabetes between migrant Asians and Caucasians in Leicester, UK. Diab Res Clin Pract 1991; 14: 205–213.
19. Hoy W, Kelly A, Jacups S, et al. Stemming the tide: reducing cardiovascular disease and renal failure in Australian Aborigines. Aust N Z J Med 1999; 29: 480–483.
20. Howard B V, Lee E T, Cowan L D, et al. Rising tide of cardiovascular disease in American Indians. The Strong Heart Study. Circ 1999; 99: 2389–2395.
21. Dobryszycka W. Biological functions of haptoglobin-new pieces to an old puzzle. Eur J Clin Chem 1997; 35: 647–654.
22. Bowman B H, Kurosky A. Haptoglobin: the evolutionary product of duplication, unequal crossing over, and point mutation. Adv Hum Gen 1982; 12: 189–261.
23. Langlois M R, Delanghe J R. Biological and clinical significance of haptoglobin polymorphism in humans. Clin Chem 1996; 42: 1589–1600.
24. Delanghe J, Langlois M, Ouyang J, Claeys G, De Buyzere M, Wuyts B. Effect of haptoglobin phenotypes on growth of *Streptococcus pyogenes*. Clin Chem Lab Med 1998; 36: 691–696.
25. Quaye I K, Ekuban F A, Goka B Q, et al. Haptoglobin 1-1 is associated with susceptibility to severe *Plasmodium falciparum* malaria. Trans R Soc Trop Med Hyg 2000; 94: 216–219.
26. Giblett E R. Genetic Markers in Human Blood. Oxford, Blackwell Scientific, 1969: 63–125.
27. Levy A P, Roguin A, Marsh S, et al. Haptoglobin phenotype and vascular complications in diabetes. N Eng J Med 2000; 343: 369–370.
28. Nakhoul F, Marsh S, Hochberg I, Leibu R, Miller B, Levy A P. Haptoglobin phenotype and diabetic retinopathy. JAMA 2000; 284: 1244–1245.
29. Nakhoul F, Zoabi R, Kantor Y, et al. Haptoglobin phentotype and diabetic nephropathy. Diabetologia 2001; in press.
30. Roguin A, Hochberg I, Nikolsky E, et al. Haptoglobin phenotype as a predictor of restenosis after percutaneous transluminal coronary angioplasty. Am J Card 2001; 87: 330–332.
31. Delanghe J, Cambier B, Langlois M, et al. Haptoglobin polymorphism, a genetic risk factor in coronary artery bypass surgery. Atheroscler 1997; 132: 215–219.
32. Chapelle J P, Albert A, Smeets J P, Heusghem C, Kulbertus H E. Effect of the haptoglobin phenotype on the size of a myocardial infarct. N Eng J Med 1982; 307: 457–463.
33. Delanghe J R, Duprez D A, De Buyzere M L, et al. Haptoglobin polymorphism and complications in established essential arterial hypertension. J Hyper 1993; 11: 861–867.
34. Surya Prabha P, Padma T, Ramaswamy M. Haptoglobin patterns in essential hypertension and associated conditions-increased risk for Hp 2-2. Hum Herid 1987; 37: 345–348.
35. Golabi P, Kshatriya G K, Kapoor A K. Association of genetic markers with coronary heart disease (myocardial infarction)-a case-control study. J Ind Med Assoc 1999; 97: 6–7.
36. Hong S H, Kang B Y, Lim J H, et al. Haptoglobin polymorphism in Korean patients with cardiovascular disease. Hum Herid 1997; 47: 283–287.
37. Bilgrami G, Tyagi S P, Qasim A. Serum haptoglobin in cases of ischemic heart disease. Jpn Heart J 1980; 21: 505–510.
38. Frohlander N, Johnson O. Haptoglobin groups in acute myocardial infarction. Hum Herid 1989; 39: 345–350.
39. Lee E T, Welty T K, Fabsitz R, et al. The Strong Heart Study: a study of cardiovascular disease in American Indians: design and methods. Am J Epid 1990; 132: 1141–1155.
40. Howard B V, Welty T K, Fabsitz R, et al. Risk factors for coronary heart disease in diabetic and nondiabetic North Americans: the Strong Heart Study. Diabetes 1992: 41: 4–11.
41. WHO Expert Committee on Diabetes Mellitus. Second Report. Geneva, World Health Organization. 1980 (technical report series 646).
42. Lee E T, Cowan L D, Howard W J, et al. All cause mortality and cardiovascular disease mortality I 3 American Indian populations aged 45 to 74 years, 1984 to 88: the Strong Heart Study. Am J Epidem 1998; 147: 995–1008.
43. Howard B V, Lee E T, Cowan L D, et al. Coronary heart disease prevalence and its relation to risk factors in American Indians: the Strong Heart Study. Am J Epidem 1995; 142: 254–268.
44. Linke R P. Typing and subtyping of haptoglobin from native serum using disc gel electrophoresis in alkaline buffer: application to routine screening. Anal Biochem 1984; 141: 55–61.
45. Wassell J, Keevil B. A new method for haptoglobin phenotyping. Ann Clin Biochem 1999; 36: 609–612.
46. Smithies O. Zone electrophoresis in starch gels: group variations in the serum proteins of normal human adults. Biochem 1955; 61: 629–641.
47. McGill M J, Donnelly R, Molyneaux L, Yue D K. Ethnic differences in the prevalence of hypertension and proteinuria in NIDDM. Diab Res Clin Pract 1996; 33: 173–179.
48. Habib G, Heibig J, Forman S, et al. Influence of coronary artery collateral vessels on myocardial infarct size in humans. Results of phase 1 thrombolysis in myocardial infarction (TIMI) trial. Circulation 1991; 83: 739–746.

49. Guigliano D, Ceriello A, Paolisso G. Oxidative stress and diabetic vascular complications. Diab Care 1996; 19: 257–267.
50. Nishikawa T, Edelstein D, Brownlee M. The missing link: a single unifying mechanism for diabetic complications. Kid Int 2000; 58 (S77): S26–S30.
51. Kristiansen M, Graversen J H, Jacobsen C, et al. Identification of the hemoglobin scavenger receptor. Nature 2001; 409: 198–201.
52. Resnick D, Pearson A, Krieger M. The SRCR superfamily: a family reminiscent of the Ig superfamily. Trends Biochem Sci 1994; 19: 5–8.
53. Nathan C F, Murray H W, Cohn Z A. Current concepts: the macrophage as an effector cell. N Eng J Med 1980; 303: 622–626.
54. Goldstein J L, Ho Y K, Basu S K, Brown M S. Binding site of macrophages that mediates uptake and degradation of acetylated low-density lipoprotein, producing massive cholesterol deposition. Proc Natl Acad Sci USA 1979; 76: 333–337.
55. Rosenfeld M E, Khoo J C, Miller E, Parthasarthy S, Palinski W, Witzum J L. Macrophage-derived foam cells freshly isolated from rabbit atherosclerotic lesions degrade modified lipoproteins, promote oxidation of low-density lipoproteins, and contain oxidation specific lipid protein adducts. J Clin Invest 1990; 87: 90–99.
56. Van den Heuvel M M, Tensen C P, van As J H, et al. Regulation of CD163 on human macrophages: cross-linking of CD163 induces signaling and activation. J Leuk Biol 1999; 66: 858–866.
57. Wagner L, Gessl A, Baumgartner Parzer S, Base W, Waldhausl W, Pasternack M S. Haptoglobin phenotyping by newly developed monoclonal antibodies. Demonstration of haptoglobin uptake into peripheral blood neutrophils and monocytes. J Imm 1996; 156: 1989–1996.
58. El Ghmati S M, Van Hoeyveld E M, Van Strijp J A G, Ceuppens J L, Stevens E A M. Identification of haptoglobin as an alternative ligand for CD11b/CD18. J Imm 1996; 156: 2542–2552.
59. Chia M C. The role of adhesion molecules in atherosclerosis. Crit Rev Clin Lab Sci 1998; 35: 573–602.
60. Epstein S E, Zhu J, Burnett M S, Zhou Y F, Vercellotti G, Hajjar D. Infection and atherosclerosis: potential roles of pathogen burden and molecular mimicry. Art Thromb Vasc Biol 2000; 20: 1417–1420.

What is claimed is:

1. A method of evaluating a risk of a diabetic patient to develop atherosclerotic cardiovascular disease (CVD), the method comprising determining a haptoglobin phenotype of the diabetic patient and thereby evaluating the risk of the diabetic patient to develop the atherosclerotic cardiovascular disease (CVD), wherein the risk is decreased in diabetic patients with haptoglobin 1-1 phenotype as compared to patients with haptoglobin 1-2 or haptoglobin 2-2 phenotypes.

2. The method of claim 1, wherein said step of determining said haptoglobin phenotype comprises determining a haptoglobin genotype of the diabetic patient.

3. The method of claim 2, wherein said step of determining said haptoglobin genotype of the diabetic patient comprises a method selected from the group consisting of a signal amplification method, a direct detection method and detection of at least one sequence change.

4. The method of claim 3, wherein said signal amplification method amplifies a molecule selected from the group consisting of a DNA molecule and an RNA molecule.

5. The method of claim 3, wherein said signal amplification method is selected from the group consisting of PCR, LCR (LAR), Self-Sustained Synthetic Reaction (3SR/NASBA) and Q-Beta (Qβ) Replicase reaction.

6. The method of claim 3, wherein said direct detection method is selected from the group consisting of a cycling probe reaction (CPR) and a branched DNA analysis.

7. The method of claim 3, wherein said detection of at least one sequence change employs a method selected from the group consisting of restriction fragment length polymorphism (RFLP analysis), allele specific oligonucleotide (ASO) analysis, Denaturing/Temperature Gradient Gel Electrophoresis (DGGE/TGGE), Single-Strand Conformation Polymorphism (SSCP) analysis and Dideoxy fingerprinting (ddF).

8. The method of claim 1, wherein said step of determining said haptoglobin phenotype comprises directly determining the haptoglobin phenotype of the diabetic patient.

9. The method of claim 8, wherein said step of determining said haptoglobin phenotype is effected by an immunological detection method.

10. The method of claim 9, wherein said immunological detection method is selected from the group consisting of a radio-immunoassay (RIA), an enzyme linked immunosorbent assay (ELISA), a western blot, an immunohistochemical analysis, and fluorescence activated cell sorting (FACS).

SEQUENCE LISTING

<160> NUMBER OF SEQ ID NOS: 1

<210> SEQ ID NO 1
<211> LENGTH: 21
<212> TYPE: PRT
<213> ORGANISM: human
<220> FEATURE:
<223> OTHER INFORMATION: haptoglobin peptide alpha 2 chain

<400> SEQUENCE: 1

Ala Val Gly Asp Lys Leu Pro Glu Cys Glu Ala Asp Asp Gly Gln Pro
                5                   10                  15

Pro Pro Lys Cys Ile
            20

11. The method of claim 1, wherein the risk of a diabetic patient to develop the atherosclerotic cardiovascular disease is decreased in diabetic patients with haptoglobin 1-1 phenotype as compared to patients with haptoglobin 1-2 phenotype, and further decreased in diabetic patients with haptoglobin 1-1 phenotype as compared to patients with haptoglobin 2-2 phenotype.

* * * * *